United States Patent
Nguyen et al.

(10) Patent No.: US 6,436,436 B1
(45) Date of Patent: *Aug. 20, 2002

(54) AQUEOUS CARRIER SYSTEMS FOR WATER-INSOLUBLE AROMATIC POLYMERS

(75) Inventors: Nghi Van Nguyen, Edison, NJ (US); David W. Cannell, New York, NY (US)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/328,384

(22) Filed: Jun. 9, 1999

(51) Int. Cl.[7] .......................... A61K 9/127; A61K 7/00; A61K 7/06
(52) U.S. Cl. ...................... 424/450; 424/401; 424/70.1; 424/70.2; 424/70.11; 424/70.21; 424/70.22; 424/73; 514/881; 514/937
(58) Field of Search .................................. 424/401, 450, 424/70.1, 70.2, 70.11, 70.21, 70.22, 73; 516/881, 937

(56) References Cited

U.S. PATENT DOCUMENTS

| | | |
|---|---|---|
| 4,174,296 A | 11/1979 | Kass |
| 4,832,872 A | 5/1989 | Scandel |
| 4,874,553 A | 10/1989 | Hager et al. |
| 5,002,761 A | 3/1991 | Mueller et al. |
| 5,160,739 A * | 11/1992 | Kanga ........................ 424/401 |
| 5,173,303 A | 12/1992 | Lau et al. |
| 5,783,554 A * | 7/1998 | Li ................................ 510/488 |

FOREIGN PATENT DOCUMENTS

| | | |
|---|---|---|
| EP | 123 071 | 10/1984 |
| EP | 340 592 | 11/1989 |
| EP | 0 596 465 A1 | 5/1994 |
| EP | 0 605 951 A1 | 7/1994 |
| EP | 868 898 A1 | 10/1998 |
| FR | 2 783 709 | 3/2000 |
| GB | 2072 508 A | 10/1981 |
| WO | WO 98/56333 | 12/1998 |

OTHER PUBLICATIONS

English Translation of EP 0 897 718, previously submitted.
International Search Report dated Oct. 20, 2000.
Ribosa et al., "Physico–chemical Modifications of Liposome Structures Through Interaction With Surfactants," *International Journal of Cosmetic Science*, pp. 131–149 (1992).

* cited by examiner

Primary Examiner—Gollamudi S. Kishore
(74) Attorney, Agent, or Firm—Finnegan, Henderson, Farabow, Garrett & Dunner, L.L.P.

(57) ABSTRACT

A composition containing at least one organic phospholipid capable of forming bilayers in aqueous solution; at least one amphoteric surfactant present in an amount by weight equal to or greater than the amount of the phospholipid; at least one nonionic surfactant present in an amount by weight equal to or greater than the amount of the phospholipid; and a water-insoluble polymer comprising at least one aromatic monomeric residue, wherein said aromatic monomeric residue comprises at least one aromatic unit substituted with at least one hydroxyl group. The invention also relates to a delivery system for water-insoluble ingredients containing the above components, and an aqueous phase, wherein the organic phospholipid, amphoteric surfactant, and nonionic surfactant are present in a combined amount sufficient to allow the water-insoluble polymer to be incorporated into the system. A method of treating a keratinous substance is also disclosed.

56 Claims, 1 Drawing Sheet

AQUEOUS CARRIER SYSTEMS FOR WATER-INSOLUBLE AROMATIC POLYMERS

The present invention relates to novel carrier systems based on organic phospholipids capable of forming bilayers in aqueous solution, amphoteric surfactants, and nonionic surfactants, wherein these carrier systems allow water-insoluble polymers to be incorporated into aqueous solutions.

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphiphatic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods utilize alcohol for cosolubilization. Alcohol solutions can have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. Ribosa et al., in "Physico-chemical modifications of liposome structures through interaction with surfactants," Int'l Journal of Cosmetic Science 14:131–149(1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, these phospholipids are toxicologically safe. It would thus be desirable for cosmetic and pharmaceutical applications to provide delivery systems that include such organic phospholipids as a carrier for other lipophilic ingredients, without the need for alcohols and other similar solvents.

In addition to solubilizing lipophilic ingredients such as oils, vitamins, and ceramides in aqueous systems, it would be desirable to solubilize other water-insoluble ingredients, specifically unneutralized or partially neutralized polymers, resins, or latexes, in aqueous delivery systems. U.S. Pat. No. 5,391,368 to Gerstein teaches solubilization of a hair-styling polymer in a composition comprising an anionic surfactant and an amphoteric surfactant. According to Gerstein, it is the amphoteric surfactant which dissolves the water-insoluble styling polymer because the polymer is not soluble in the anionic surfactant alone.

Gerstein presents some problems, however. Many hair care and hair setting products are formulated at acidic pH because of a desire for such products to be compatible with the pH of the scalp and hair surface. Gerstein does not disclose a pH at which its system is formulated, but if the Gerstein system is acidified, the polymer will precipitate out of solution. In addition, the Gerstein system does not carry and there is no suggestion that it could carry any additional lipophilic ingredients in its mixture of anionic surfactant, amphoteric surfactant, and styling polymer. Further, Gerstein does not describe the incorporation of its styling polymer into any products other than the disclosed styling shampoo, nor does Gerstein suggest that such incorporation would be possible.

Thus, there remains a need for an aqueous delivery system that can solubilize water-insoluble materials in such a manner that they will not precipitate out of solution upon acidification, where the amount of deposition of water-insoluble material can be controlled, and where the system could carry other ingredients in addition to the water-insoluble ingredient. For example, it would be beneficial to have a system which incorporates water-insoluble materials into compositions containing other ingredients, such as dyeing and permanent wave compositions. The present invention provides such a delivery system.

In order to achieve these and other advantages, the present invention is drawn to a composition made up of at least one organic phospholipid capable of forming bilayers in aqueous solution, at least one amphoteric surfactant, at least one nonionic surfactant and at least one water-insoluble polymer comprising at least one aromatic monomeric residue, wherein the aromatic monomeric residue comprises at least one hydroxyl substituted aromatic group. The amphoteric surfactant and the nonionic surfactant are each present in an amount equal to or greater than the amount of the organic phospholipid. The phospholipid, amphoteric surfactant, and nonionic surfactant are present in a combined amount sufficient to allow at least one water-insoluble polymer to be incorporated into an aqueous solution. The water-insoluble polymers used in the invention contain at least one aromatic monomeric residue having at least one aromatic group substituted with at least one hydroxyl group.

In another embodiment, the present invention relates to an aqueous delivery system for water-insoluble materials. The delivery system (or "carrier") includes the above-described composition and an aqueous phase. The amphoteric surfactant and the nonionic surfactant are each present in an amount equal to or greater than the amount of the organic phospholipid. The organic phospholipid, the amphoteric surfactant, and the nonionic surfactant are present in a combined amount sufficient to allow the water-insoluble polymer comprising at least one aromatic monomeric residue, wherein the aromatic monomeric residue comprises at least one hydroxyl substituted aromatic group to be incorporated into or solubilized by the delivery system. The present invention is also drawn to a process for the preparation of an aqueous system comprising: (a) combining at least one organic phospholipid capable of forming bilayers in aqueous solution, at least one amphoteric surfactant, and at least one nonionic surfactant to form a mixture, (b) heating the mixture obtained in step (a), (c) adding an aqueous solution to form a diluted mixture, and (d) cooling the diluted mixture. The water-insoluble polymer comprising at least one aromatic monomeric residue can be incorporated in step (a).

Finally, in yet another embodiment, the present invention is drawn to a method for treating keratinous substances such as skin, hair, or eyelashes. First an aqueous solution is prepared containing at least one organic phospholipid capable of forming bilayers in aqueous solution; at least one amphoteric surfactant present in an amount equal to or greater than the amount of the organic phospholipid; at least one nonionic surfactant present in an amount by weight equal to or greater than the amount of the phospholipid; and at least one water-insoluble polymer comprising at least one aromatic monomeric residue, as described above. The phospholipid, amphoteric surfactant, and nonionic surfactant are present in a combined amount sufficient to allow the water-insoluble polymer comprising at least one aromatic monomeric residue to be incorporated into the aqueous solution. The aqueous solution is then applied to the keratinous substances.

Reference will now be made in detail to the present preferred embodiment(s) of the invention.

Advantageously, the present invention allows water-insoluble materials or ingredients to be solubilized in an aqueous solution. No alcohol is required for cosolubilization, and there is no need for liposome preparation. Further, when the water evaporates, the residue left behind includes the water-insoluble material and/or the phospholipid.

The composition of the invention is also easy to formulate and is gentle on the hair, skin, or eyelashes because the surfactants used are generally mild. Unlike the attempted solubilization of phospholipids in the prior art, the preferred embodiment of the present invention requires the presence of at least one amphoteric surfactant and at least one nonionic surfactant in the concentrated solutions of phospholipid.

The compositions and delivery systems of the present invention readily deposit the organic phospholipid/water-insoluble substances on the hair, skin, and eyelashes, and, because of their inherent insolubility, resist being washed off with water. Accordingly, these compositions and delivery systems can be used in hair shampoos, conditioners, hair dyeing compositions, including oxidative dyes and bleaches, permanent waving compositions, curl relaxing compositions, hair setting compositions, bath and body products, sunscreens, or cosmetics such as mascaras and foundations.

These systems can also be used to deliver active water-insoluble pharmaceutical ingredients, particularly in topical applications. Such systems could further help protect against oxidation and rancidity by protecting sensitive ingredients in pharmaceuticals or foods.

Additionally, the "load" carried by these systems can be quite high, a benefit that inures both to the user and to the manufacturer in an economic sense. Load is defined as the weight of added hydrophobe (water-insoluble material) divided by the weight of the phospholipid expressed as a percentage. Thus, 1 g of hydrophobe in a composition with 5 g phospholipid is a ⅕ or 20% load. In the art, 50% is considered a high load and can be achieved with certain hydrophobes and surfactant combinations.

Without being bound to a particular theory, the inventors believe that in the composition of the present invention, an organized structure, likely a laminar gel, is formed between the organic phospholipid and the nonionic surfactant and is solubilized by the amphoteric surfactant. The organized structure can incorporate other water-insoluble materials or hydrophobes. In aqueous systems, the structure remains organized, as evidenced by the clarity of the solution, exhibiting a slight Tyndall light scattering effect, and, when concentrated, showing lamellar anisotropic structures under polarized light.

In one embodiment, therefore, the invention is drawn to a composition comprising at least one organic phospholipid capable of forming bilayers in aqueous solution, at least one amphoteric surfactant, and at least one nonionic surfactant, where the amphoteric surfactant and nonionic surfactants are each present in an amount by weight equal to or greater than the amount of the phospholipid. Neither the amphoteric nor the nonionic surfactant alone will give a satisfactory solution with the organic phospholipids. When dissolved in either an amphoteric or a nonionic surfactant, solubility for the phospholipid was usually poor compared to solubility in the mixture of surfactants of the present invention.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

In the present invention, lecithin is preferably used in an amount greater than 0 to about 5% by weight of the composition as a whole. Since lecithin itself is not a pure raw material and may have free glycerides, glycerin, fatty acids, and soaps, adjustments in this ratio may need to be made, i.e., one source of lecithin may require different ratios of nonionic and amphoteric surfactants than another to achieve maximum clarity of solution. Preferably, the composition of the invention forms a clear solution, though the purpose of the invention is achieved just as effectively with a slightly cloudy solution.

Other than lecithins, another group of phospholipids which may be useful in the present invention is multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Cocamphodipropionate is particularly preferred, for example, MIRANOL C2M-SF Conc. (disodium cocamphodipropionate), in its salt-free form, available from Rhône-Poulenc. Also preferred is CROSULTAINE C-50 (cocamidopropyl hydroxysultaine), available from Croda. Other amphoteric surfactants useful in the present invention include disodium wheatgermimido PEG-2 sulfosuccinate, available under the trade name MACKANATE WGD from McIntyre Group Ltd. and disodium soyamphodiacetate, available under the trade name MACKAM 2S from McIntyre Group Ltd.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

| # of C's | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | Arlasolve 200, available from ICI Surfactants |
| C-18 | Steareth-10 | Volpo S-10, available from Croda Chemicals Ltd. |
| C-18 | Steareth-16 | Solulan-16, available from Amerchol Corp. |
| C-18 | Steareth-20 | BRIJ 78, available from ICI Surfactants |
| C-18 | Steareth-25 | Solulan-25, available from Amerchol Corp. |
| C-18 = | Oleth-10 | BRIJ 97, available from ICI Surfactants |
| C-18 = | Oleth-20 | Volpo-20, available from Croda Chemicals Ltd. |

Alkyl polyglucose surfactants sold under the name PLANTAREN, available from Henkel, may also be used.

In one preferred embodiment of the composition of the present invention, the organic phospholipid capable of forming bilayers in aqueous solution, the amphoteric surfactant, and the nonionic surfactant are present in the composition such that the nonionic surfactant and the amphoteric surfactant are each present in an amount by weight greater than the amount of phospholipid. In a more preferred embodiment, the amount of phospholipid in the composition is kept fixed while the amounts of the amphoteric and nonionic surfactants are increased. In a still more preferred embodiment, calculating the phospholipid as present at a value of 1, the phospholipid, amphoteric surfactant and nonionic surfactant are preferably present in the composition in a ratio ranging from about 1:2:2 and above by weight, i.e., where the amounts of the surfactants can be increased independently of each other but the amount of phospholipid stays fixed. The ratio is considered to be "above" 1:2:2 when the amount of either of the surfactants increases. When the phospholipid/ amphoteric/nonionic system is employed as a carrier for a water-insoluble polymer, the ratio is preferably about 1:3:3 and above, and more preferably above about 1:3:4. The loading capability for hydrophobes carried by the delivery system of the present invention is maximized if the ratio of nonionic surfactant to phospholipid is minimized, with the bilayers still being solubilized, because an excess of nonionic surfactant may disrupt the organized structure.

In one preferred embodiment, the composition of the present invention comprises ALCOLEC S (soy lecithin), MIRANOL C2M-SF Conc. (disodium cocamphodipropionate, an amphoteric surfactant), ARLA-SOLVE 200(IsoCeteth-20, a nonionic surfactant) in a ratio of 5:15:20(1:3:4) wherein the ratios are calculated by weight. In general, the preferred compositions of the invention are known as the "LAN" because they contain a lecithin (L), an amphoteric surfactant (A), and a nonionic surfactant (N). Although lecithin is particularly preferred, the amphoteric and nonionic surfactants may vary. The "LAN" itself is disclosed in WO 98/56333, the disclosure of which is hereby incorporated by reference, but its use with the specific water-insoluble polymer of the present invention is not disclosed.

When used as an ingredient in further formulations, the LAN is compatible and generally gives clear solutions with anionic surfactants such as alkyl sulfates and ethoxylated alkyl sulfates. Other anionic surfactants such as sulfosuccinates may also be used. Typically, LAN compositions are stable and can resist storage at 45° C. for three months or more, which would predict that they have a shelf life at room temperature of at least three years.

In another aspect, the present invention relates to an aqueous delivery or carrier system comprising: at least one organic phospholipid capable of forming bilayers in aqueous solution, at least one amphoteric surfactant present in an amount greater than or equal to the amount of the phospholipid, at least one nonionic surfactant present in an amount greater than or equal to the amount of the phospholipid, at least one water-insoluble polymer comprising at least one aromatic monomeric residue which comprises at least one aromatic group substituted with at least one hydroxyl group, and an aqueous phase. The organic phospholipid amphoteric surfactant, and nonionic surfactant are present in a combined amount sufficient to allow the at least one water-insoluble polymer to be incorporated into or solubilized by the aqueous system. The amount sufficient for solubilization may vary depending on the type of composition; for example, shampoo and mascara formulations require a lower concentration of LAN than do conditioner, deep treatment, bleach, permanent wave, dye, and relaxant compositions.

In the delivery system, the organic phospholipid, preferably lecithin, is preferably present in an amount greater than 0 to about 5% by weight of the delivery system as a whole. More preferably, the lecithin is present in an amount ranging from about 0.1 to about 0.3% by weight. Since lecithin itself is not a pure raw material and may glycerides, glycerin, fatty acids, and soaps, adjustments in this ratio may need to be made, i.e., one source of lecithin may require different ratios of amphoteric and nonionic surfactants than another to achieve maximum clarity of solution. Preferably, the composition of the invention forms a clear solution, though the purpose of the invention is achieved just as effectively with a slightly cloudy solution.

The at least one amphoteric surfactant is preferably present in the system of the invention in an amount ranging from about 5 to 25% by weight of the delivery system as a whole when 5% of the organic phospholipid, preferably lecithin, is used. When the phospholipid/amphoteric/ nonionic system is employed as a carrier for a water-insoluble polymer, the amphoteric surfactant is preferably present in an amount ranging from about 15 to 25% by weight.

The at least one nonionic surfactant is preferably present in an amount of about 5 to 20% by weight relative to the weight of the delivery system when 5% lecithin is used.

More preferably, the nonionic surfactant is present in an amount of about 10 to 20% by weight.

The water-insoluble polymers used in the present invention are comprised of aromatic monomeric residues or repeating units, wherein the aromatic monomeric residues are substituted on the aromatic moiety with at least one hydroxyl group and preferably, the water-insoluble polymer is protein-adherent. See EP 0 605 951 A1, the disclosure of which is hereby incorporated by reference. An aromatic monomeric residue is a monomeric residue that has a resonance stabilized, conjugated ring system. In a preferred embodiment, the ring structure is planar, and in a further preferred embodiment, the aromatic moiety is a phenyl group. The polymers comprising the aromatic monomeric residues may be copolymers such as a random copolymer, a block copolymer, or a graft copolymer. Preferably, the water-insoluble polymers comprising aromatic monomeric residues do not contain carboxyl moieties.

Preferred aromatic monomeric residues of the protein-adherent water insoluble polymers include hydroxyphenyl-containing groups and more preferably para-hydroxyphenyl groups such as 4-hydroxystyrene. Other substitutions on the aromatic monomeric residues including the aromatic moiety are also within the practice of the invention.

Preferably, the water-insoluble polymer comprised of aromatic monomeric residues is a polyhydroxystyrene (PHS) polymer. A PHS polymer is a protein-adherent, linear or branched polymer that contains hydroxystyrene monomeric residues and does not contain a carboxylic acid group. One type of PHS polymer, poly(p-hydroxystyrene), is a linear vinyl or branched polymer comprised of p-hydroxystyrene monomeric residues. Poly-(p-hydroxystyrene) is also referred to as a homopolymer of 4-ethenylphenol.

The following are examples of PHS polymers, available from TriQuest, LP, of Dallas, Tex, that can be incorporated into the delivery system of the present invention. The list is not intended to be limiting:

PHS-E: poly-(p-hydroxystyrene) Electronic Grade is a linear vinyl polymer formed from the polymerization of p-acetoxystyrene monomer to poly-(p-acetoxystyrene) (PAS) and subsequent hydrolysis to PHS. PHS-E is a 100% linear styrenic backbone polymer commercially available in molecular weights from 8,000 to 100,000 and is comprised of the repeating units of formula (I) below:

(I)

where n is the number of repeating units.

PHS-PG: poly-(p-hydroxystyrene) Polymer Grade is a direct product from the dehydration of p-hydroxyphenyl methyl carbinol (HPMC). This PHS polymer is a mixture of vinyl linear and branched polymer which may be represented by formula (II) below:

where n is the number of repeating units.

PHS-N: poly-(p-hydroxystyrene) Novolak Grade is fully branched with no styrenic backbone character in the polymer. As shown in formula (III) below, PHS-N is a linear polymer with branched units positioned ortho to the -OH functional group.

(III)

where n is the number of repeating units.

PHS-PG-L: poly-(p-hydroxystyrene) Polymer Grade Linear has the same 100% styrenic backbone as PHS-E, formula (I) above. PHS-PG-L is produced via the free radical polymerization from hydroxystyrene monomer (HSM) which lends itself to the production of a wide variety of developing co- or ter- polymers with other unsaturated monomers at a wide range of monomer ratios.

PHS-BZT: poly-p-hydroxystyrene Benzotriazole is a polymeric benzotriazole of formula (IV) below that can be used as a UV absorber and stabilizer in polymers.

(IV)

wherein R=

X = H or and m and n are the number of repeating units.

Up to 3% by weight, relative to the weight of the delivery system, of a PHS polymer was dissolved in phospholipid/amphoteric surfactant/nonionic surfactant solutions where the phospholipid was lecithin and the ratio of lecithin:amphoteric:nonionic was 1:3:4. All the solutions were clear, indefinitely dilutable with water without precipitation and stable. A higher weight percentage of PHS polymer may be dissolved in a phospholipid/amphoteric surfactant/nonionic surfactant solution by adjusting the ratios and/or the surfactants or phospholipid chosen to make up the aqueous carrier system.

PHS polymers and other water-insoluble polymers comprising aromatic monomeric residues offer numerous advantages for use in cosmetic, hair care, and pharmaceutical compositions including but not limited to: protein adherent properties, such as the ability to adhere to keratinous substances, such as hair, skin, and nails; and UV absorption properties which may be used in protective sun screens and lotions or hair protectants. A composition comprising at least one organic phospholipid capable of forming bilayers in aqueous solution, at least one amphoteric surfactant, at least one nonionic surfactant, and at least one water-insoluble polymer comprising aromatic monomeric residues also imparts protecting and conditioning effects on keratinous fibers such as hair. For example, treatment of hair with a LAN/PHS composition protects the hair cuticle from protein loss in addition to easing the ability to comb, i.e., combability of hair.

The aqueous phase of the inventive delivery system can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

If the inventive system is to be used in concentrated form, i.e., with about 5% by weight of the organic phospholipid and 1% of added water-insoluble polymer, the composition preferably has a pH ranging from 4–12 for maximum stability and clarity. The more concentrated the solution, the better the delivery.

If this blend is diluted with water or the blend is used as an ingredient in another composition, then the pH has a broader range, i.e., preferably ranges from 2–12, and a wider variety of additives can be included in the solution. When water is added to a concentrated LAN, it may appear to form a cloudy solution at first if a large amount of water is added at once. The LAN will eventually go into solution, however, and become clear or at least clearer. The time to clear decreases as the LAN ratio increases. Once the organized structure of the LAN forms, the addition of more water does not affect clarity. These dilute blends are still very effective in delivering water-insoluble ingredients. The blends can be freeze-dried to hygroscopic solids that redissolve into water. Encapsulation of such solids so that they do not pick up and retain excess moisture is also contemplated. Such encapsulated solids can have desirable storage properties and would be easy to dissolve into water at various dilutions. Understandably, the need for dilution varies depending on the water-insoluble material to be employed.

Another embodiment of the present invention is drawn to a process for preparing the aqueous system of the present invention. This process comprises: (a) combining the following ingredients to obtain a mixture: at least one organic phospholipid capable of forming bilayers in aqueous solution, at least one amphoteric surfactant, and at least one nonionic surfactant, where the nonionic surfactant and amphoteric surfactant are each present in an amount by weight equal to or greater than the amount of the organic phospholipid, (b) heating the mixture obtained in step (a), and (c) adding an aqueous solution to the heated mixture to obtain the desired carrier system. Water-insoluble ingredients may be added in step (a). Preferably the carrier system obtained can carry a high load (i.e., 50% is considered a high load) of the organic phospholipid/water-insoluble ingredient. The mixture is preferably heated at a temperature of 65° C. to 85° C., depending on the melting points of the solid surfactants.

More specifically, the preparation of the carrier system of the present invention may be carried out as follows. Lecithin (L) is dispersed in water. The water-insoluble polymer is combined with nonionic surfactant(s) (N) at appropriate ratios and added to the lecithin/water dispersion. An amphoteric surfactant (A) is added and the mixture is heated, preferably to a temperature of about 70° C. The combination of these ingredients results in a solution which is clear to slightly hazy and is referred to as the "LAN," which can then be used as a "raw material" to make finished products.

Alternatively, lecithin, amphoteric surfactant(s) and nonionic surfactant(s) can be weighed to appropriate ratios, combined, and stirred at 70° C. The water-insoluble polymer is added and the resulting solution is stirred further. Water is then added at a quantity sufficient (q.s.) at the same temperature. Another alternative method of preparation comprises adding the water-insoluble ingredient with mixing after solutions have cooled. This last alternative method helps protect heat-sensitive water-insoluble ingredients.

Another process for preparing the aqueous system, also within the practice of the invention, comprises (a) dissolving the water-insoluble polymer in a basic solution, (b) combining the following ingredients to obtain a mixture: at least one organic phospholipid capable of forming bilayers in aqueous solution, at least one amphoteric surfactant, and at least one nonionic surfactant, where the amphoteric surfactant and nonionic surfactant are each present in an amount by weight equal to or greater than the amount of the organic phospholipid, (c) heating the mixture obtained in step (b) and combining it with solution obtained in step (a). The mixture is preferably heated at a temperature of 65° C. to 85° C., depending on the melting points of the solid surfactants. The resulting solution may also be acidified.

In a preferred embodiment a PHS polymer is dissolved in a basic solution.

Lecithin (L) is dispersed in water. The nonionic surfactant(s) (N) is added to the lecithin/water dispersion. An amphoteric surfactant (A) is added and the mixture is heated, preferably to a temperature of from 70° C. to 85° C. to form the LAN. The PHS solution is then added to the LAN and the resulting mixture is acidified. The system can then be used as a "raw material" to make finished products. As noted above, the resulting compositions may vary from clear to slightly hazy and are infinitely dilutable with water.

In another embodiment, the present invention is drawn to a method for treating keratinous substances such as, but not limited to, hair, skin, or eyelashes. First an aqueous solution is prepared containing at least one organic phospholipid capable of forming bilayers in aqueous solutions; at least one amphoteric surfactant present in an amount by weight greater than or equal to the amount of the phospholipid; at least one nonionic surfactant present in an amount by weight equal to or greater than the amount of the phospholipid; and at least one water-insoluble polymer as described above. The phospholipid, amphoteric surfactant, and nonionic surfactant are present in a combined amount sufficient to allow the water-insoluble polymer to be incorporated into the aqueous solution. The aqueous solution is then applied to the keratinous substances. The term "treating" in the context of this invention includes, but is not limited to, shampooing, conditioning, dyeing, bleaching, permanent waving, relaxing, setting, moisturizing, and making-up, for example, applying mascara or foundation.

As mentioned previously, the composition and carrier system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

With respect to hair products, the carrier system of the present invention can be used to formulate hair products, e.g., for normal hair, color-treated hair, dry hair, fine hair, and damaged hair. For each type of hair, the LAN can be used to create a regimen comprising shampoo, conditioner, and deep treatment, (i.e., deep conditioner). Additional nonionic, amphoteric, and also anionic surfactants can be added. In general, the concentration of the LAN is increased within each regimen from shampoo to conditioner to deep treatment. Thus, the deep treatment formulations have the most concentrated hydrophobe-carrying LAN.

The LAN systems of the invention can be further associated, in the hair products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN and enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN is treated as a water-insoluble, particularly a lipophilic, ingredient itself.

The LAN may also include lipophilic ingredients such as silicones, oil-soluble vitamins such as Vitamin E and Vitamin A, sunscreens, ceramides and natural oils. The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, and laurylmethicone copolyol. The lipophilic ingredients will, for example, moisturize or condition the skin, hair, and/or eyelashes and leave behind no oily feel.

The LAN may also include water-insoluble polymers, resins, and latexes which are unneutralized or partially neutralized, wherein the polymers and resins contain carboxyl moieties, such as acrylates and other carboxy polymers. Other ingredients in the LAN hair care compositions may include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

The invention will be further clarified by the following examples, which are intended to be illustrative of the invention, but not limiting thereof.

EXAMPLE 1

Preparation of PHS Polymer/LAN Combinations

The protein adhering properties of PHS polymers, and other aromatic polymers comprised of monomeric residues with hydroxy substituted aromatic groups, make these polymers highly desirable ingredients in hair care, skin care, mascara, and other products in which adherence to proteins, such as keratin surfaces, is desired. However, the water-insoluble nature of these polymers makes them difficult to formulate in most cosmetic or pharmaceutical formulations. The present invention enables incorporation of aromatic polymers like PHS into an aqueous system that is indefinitely dilutable and stable over a variety of pH.

a. Incorporation of PHS-N into LAN 5 g of lecithin was combined with 15 g of MIRANOL 2CM-SF (disodium cocamphodipropionate) and 20 g of ARLASOLVE 200(PEG-20 Isocetyl Ether) and stirred at 70° C. for 15 minutes. 3 g of PHS-N was added to the clear solution and the resulting solution was stirred for an additional 15 minutes. More water was added and the solution was stirred at 70° C. for another 30 minutes until homogeneous. The LAN/PHS-N solution was dilutable indefinitely with water. Upon acidification to pH 2–3 with citric acid, the solution remained clear and was still dilutable indefinitely with water. Thus, a 60% load of PHS-N or 3% of PHS-N relative to the total weight of the delivery system was achieved in the LAN/PHS-N system.

An alternative procedure to incorporate PHS-N involved the neutralization of PHS-N with a base. A solution of 3 g of PHS-N was prepared by dissolving PHS-N in 30 g or 0.5N NaOH solution. The PHS-N solution was then added to a clear LAN system at 70° C. and prepared as described above. A 60% load of PHS-N or 3% of PHS-N relative to the total weight of the delivery system was achieved and the LAN/PHS-N solution was once again dilutable indefinitely with water and remained clear upon acidification with citric acid to pH 4.

b. Incorporation of PHS-BZT into LAN

PHS-BZT was also incorporated into LAN using the second procedure described in (a) above. A solution of 0.5 g of PHS-BZT in 10 g of NaOH was added to the LAN system (5 g Lecithin, 25 g of MIRANOL 2CM-SF, 20 g of ARLASOLVE 200, and 39.5 g water). Acidification to pH 4 resulted in a clear stable gel.

EXAMPLE 2

Study of Hair Protecting Effects of the LAN System

Figure 1:
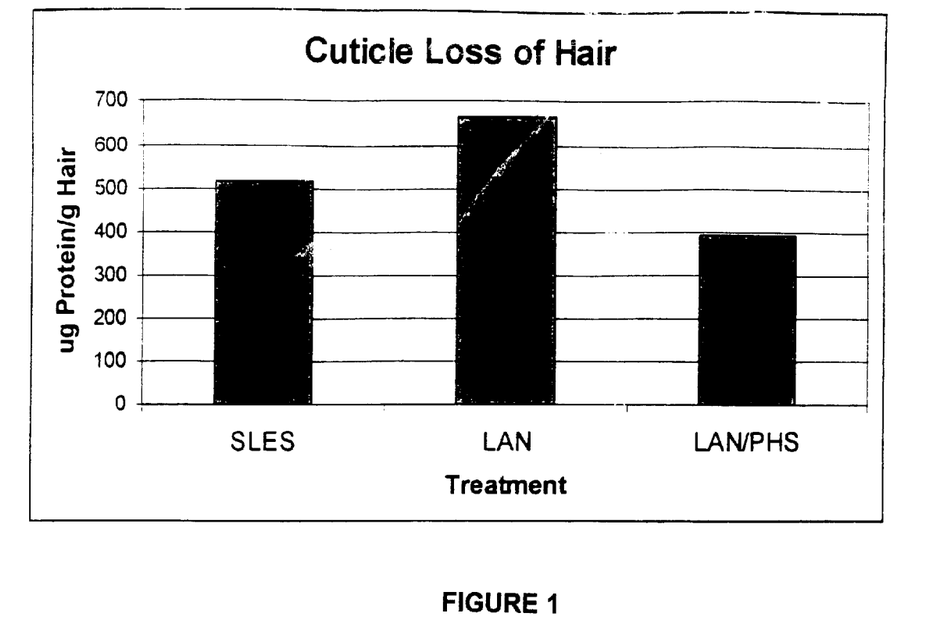
FIG. 1 is a comparison of the cuticle loss for hair treated with SLES, LAN, or LAN/PHS. The cuticle loss is determined by measuring the amount of protein lost per grams of hair treated.

Normal hair was treated with the following solutions for 1 minute at room temperature and then rinsed with warm water:
(1) 10% Sodium Laureth Sulfate (SLES)
(2) LAN (1:3:4)
(3) LAN/PHS-N (1:3:4 LAN with 3% PHS-N)
Each treatment was applied 5 times. The treated hair was then shaken in water for 10 hours The cuticle loss, represented by the protein content in the water, was determined by the Lowry method (Sigma). See Sandha et al., *J. Soc. Cosmet. Chem.*, 44, pp.163–175 (1993). The results in FIG. 1 indicate that the LAN/PHS-N treated hair lost the least protein during the mechanical shaking. The results demonstrate that the LAN system, and more preferably a LAN system containing a protein adherent water-insoluble polymer, imparts a protecting effect on the hair cuticle.

EXAMPLE 3

Study of Hair Conditioning Using the LAN System

Normal hair was treated with the following solutions for 1 minute at room temperature and then rinsed with warm water:
(1) 10% Sodium Laureth Sulfate (SLES)
(2) LAN (1:3:4)
(3) LAN/PHS-N (1:3:4 LAN with 3% PHS-N)

The treated hair was subjected to the dry combability test using the Instron Tester.

Figure 2:
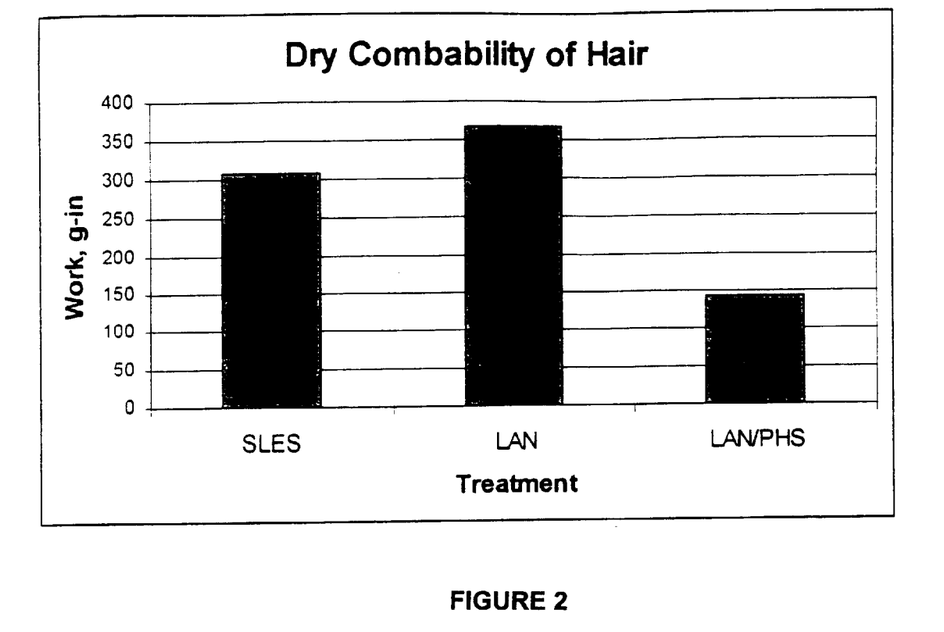
FIG. 2 is a comparison of the dry combability for hair treated with SLES, LAN, or LAN/PHS. The combability is determined by the amount of work needed to comb the treated hair.

Using the Instron Tester, the ease of combing is reflected by the amount of work needed to pull the comb through dry hair. The results, shown in FIG. 2, indicate that hair treated with the LAN/PHS-N solution is easier to comb compared to the two controls. The results demonstrate that the LAN system, and more preferably a LAN system containing a protein adherent water-insoluble polymer, imparts a conditioning effect on hair.

What is claimed is:

1. A composition comprising:

at least one phospholipid capable of forming bilayers in aqueous solution;

at least one amphoteric surfactant;

at least one nonionic surfactant present in an amount by weight equal to or greater than the amount of said at least one phospholipid; and wherein said at least one phospholipid, said at least one amphoteric surfactant, and said at least one nonionic surfactant are present in a combined amount sufficient to allow at least one water-insoluble polymer to be incorporated into an aqueous solution, and wherein said at least one water-insoluble polymer comprises at least one aromatic monomeric residue, said at least one aromatic monomeric residue comprising at least one aromatic group substituted with at least one hydroxyl group.

2. A composition according to claim 1, wherein said composition further comprises water.

3. A composition according to claim 1, wherein said at least one nonionic surfactant is present in an amount by weight greater than the amount of said at least one phospholipid.

4. A composition according to claim 1, wherein said at least one amphoteric surfactant is present in an amount by weight greater than the amount of said at least one phospholipid.

5. A composition according to claim 1, wherein said at least one phospholipid capable of forming bilayers in aqueous solution is a lecithin.

6. A composition according to claim 1, wherein said at least one water-insoluble polymer is selected from polyhydroxystyrene polymers.

7. A composition according to claim 6, wherein said polyhydroxystyrene polymers are comprising at least one p-hydroxystyrene monomeric residue and wherein said polyhydroxystyrene polymers are selected from linear, branched, and linear and branched polymers.

8. A composition according to claim 6, wherein said polyhydroxystyrene polymers are linear vinyl polymers comprising at least one monomeric residue as defined below:

9. A composition according to claim 6, wherein said polyhydroxystyrene polymers are vinyl linear and branched polymers comprising at least one monomeric residue as defined below:

10. A composition according to claim 6, wherein said polyhydroxystyrene polymers are branched polymers comprising at least one monomeric residue as defined below:

11. A composition according to claim 6, wherein said polyhydroxystyrene polymers are benzotriazole polymers comprising at least one monomeric residue as defined below:

12. A composition according to claim 1, wherein said at least one nonionic surfactant contains at least one group selected from $C_8$ to $C_{24}$ fatty alcohol, $C_8$ to $C_{24}$ fatty acid, and $C_8$ to $C_{24}$ glyceride.

13. A composition according to claim 1, wherein said at least one nonionic surfactant has an HLB of at least 10.

14. A composition according to claim 1, wherein said at least one amphoteric surfactant is selected from betaines, sultaines, hydroxysultaines, alkyl amphodiacetates, alkyl amphodipropionates, imidazolines, and salts thereof.

15. A composition according to claim 14, wherein said at least one amphoteric surfactant is selected from cocamphodipropionate and cocamidopropyl hydroxysultaine.

16. A composition according to claim 1, wherein said at least one phospholipid, said at least one amphoteric surfactant, and said at least one nonionic surfactant are present in a ratio of 1:0.8:2 and above.

17. A composition according to claim 1, wherein said at least one phospholipid, at last one amphoteric surfactant, and said at least one nonionic surfactant are present in a ratio of 1:1.2:3 and above.

18. A composition according to claim 16, wherein said at least one phospholipid, said at least one amphoteric surfactant, and said at least one nonionic surfactant are present in a ratio of 1:1.2:4 and above.

19. A delivery system for water-insoluble ingredients comprising:
  at least one phospholipid capable of forming bilayers in aqueous solution;
  at least one amphoteric surfactant;
  at least one nonionic surfactant present in an amount by weight equal to or greater than the amount of said at least one phospholipid;
  at least one water-insoluble polymer comprising at least one aromatic monomeric residue, wherein said at least one aromatic monomeric residue comprises at least one aromatic group substituted with at least one hydroxyl group; and
  an aqueous phase,
    wherein said at least one phospholipid, said at least one amphoteric surfactant, and said at least one nonionic surfactant are present in a combined amount sufficient to allow said at least one water-insoluble polymer to be incorporated into said system.

20. A delivery system for lipophilic ingredients according to claim 19, wherein said at least one amphoteric surfactant is present in an amount by weight greater than the amount of said at least one phospholipid and wherein said at least one nonionic surfactant is present in an amount by weight equal to or greater than the amount of said at least one phospholipid.

21. A delivery system according to claim 19, wherein said aqueous phase further comprises additional ingredients selected from anionic surfactants, organic salts, inorganic salts, proteins, hair dyes, water-soluble polymers, and amino acids.

22. A delivery system according to claim 19, wherein said at least one water-insoluble polymer is selected from polyhydroxystyrene polymers.

23. A delivery system according to claim 22, wherein said polyhydroxystyrene polymers comprise at least one p-hydroxystyrene monomeric residue and wherein said polyhydroxystyrene polymers are selected from linear, branched, and linear and branched polymers.

24. A delivery system according to claim 22, wherein said polyhydroxystyrene polymers are linear vinyl polymers comprising at least one monomeric residue as defined below:

25. A delivery system according to claim 22, wherein said polyhydroxystyrene polymers are vinyl linear and branched polymers comprising at least one monomeric residue as defined below:

26. A delivery system according to claim 22, wherein said polyhydroxystyrene polymers are branched polymers comprising at least one monomeric residue as defined below:

27. A delivery system according to claim 22, wherein said polyhydroxystyrene polymers are benzotriazole polymers comprising at least one monomeric residue as defined below:

28. A delivery system according to claim 19, wherein said at least one phospholipid capable of forming bilayers in aqueous solution is a lecithin.

29. A delivery system according to claim 19, wherein said at least one nonionic surfactant contains at least one group selected from $C_8$ to $C_{24}$ fatty alcohol, $C_8$ to $C_{24}$ fatty acid, and $C_8$ to $C_{24}$ glyceride.

30. A delivery system according to claim 19, wherein said at least one nonionic surfactant has an HLB of at least 10.

31. A delivery system according to claim 19, wherein said at least one amphoteric surfactant is selected from betaines, sultaines, hydroxysultaines, alkyl amphodiacetates, alkyl amphodipropionates, imidazolines, and salts thereof.

32. A delivery system according to claim 31, wherein said at least one amphoteric surfactant is selected from cocamphodipropionate and cocamidopropyl hydroxysultaine.

33. A delivery system according to claim 19, wherein said at least one phospholipid is present in an amount of greater than 0 to 5% by weight relative to the total weight of said delivery system.

34. A delivery system according to claim 33, wherein said at least one phospholipid is present in an amount of 5% by weight relative to the total weight of said delivery system.

35. A delivery system according to claim 19, wherein said at least one amphoteric surfactant is present in an amount of 5% to 25% by weight relative to the total weight of the delivery system.

36. A delivery system according to claim 35, wherein said at least one amphoteric surfactant is present in an amount of 15% to 25% by weight relative to the total weight of the delivery system.

37. A delivery system according to claim 19, wherein said at least one nonionic surfactant is present in an amount of 5% to 20% by weight relative to the total weight of the delivery system.

38. A delivery system according to claim 37, wherein said at least one nonionic surfactant is present in an amount of 10% to 20% by weight relative to the total weight of the delivery system.

39. A delivery system according to claim 19, wherein said at least one phospholipid, said at least one amphoteric surfactant, and said at least one nonionic surfactant are present in a ratio of 1:0.8:2 and above.

40. A delivery system according to claim 19, wherein said at least one phospholipid, said at least one amphoteric surfactant, and said at least one nonionic surfactant are present in a ratio of 1:1.2:3 and above.

41. A delivery system according to claim 40, wherein said at least one phospholipid, said at least one amphoteric surfactant, and said at least one nonionic surfactant are present in a ratio of 1:1.2:4 and above.

42. A delivery system according to claim 18, wherein said at least one phospholipid is a lecithin, said at least one amphoteric surfactant is disodium cocamphodipropionate, an said at least one nonionic surfactant is selected from PPG-5-Ceteth-20, PEG-20 Isocetyl Ether, and Oleth-10.

43. A delivery system according to claim 19, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

44. A delivery system according to claim 43, wherein said make-up composition is a mascara or a foundation.

45. A method for the preparation of a delivery system as claimed in claim 19, said method comprising:
(a) combining said at least one phospholipid, said at least one amphoteric surfactant, said at least one nonionic surfactant; and said at least one water-insoluble polymer comprising at least one aromatic monomeric residue to obtain a mixture;
(b) heating the mixture obtained in step (a);
(c) adding an aqueous solution to form a diluted mixture; and
(d) cooling said diluted mixture.

46. A method for the preparation of a delivery system as claimed in claim 19, said method comprising:
(a) dissolving at least one water-insoluble polymer comprising at least one aromatic monomeric residue in a solution
(b) combining said at least one organic phospholipid, said at least one amphoteric surfactant, and said at least one nonionic surfactant to obtain a mixture;
(b) heating the mixture obtained in step (b) and adding the solution obtained in step (a);
(c) adding an aqueous solution to form a diluted mixture; and
(d) acidifying and cooling said diluted mixture.

47. A method for treating a keratinous substance, said method comprising:
preparing an aqueous solution comprising
at least one phospholipid capable of forming bilayers in aqueous solution;
at least one amphoteric surfactant;
at least one nonionic surfactant present in an amount by weight equal to or greater than the amount of said at least one phospholipid; and
at least one water-insoluble polymer comprising at least one aromatic monomeric residue,
wherein said at least one aromatic monomeric residue comprises at least one aromatic group substituted with at least one hydroxyl group, wherein said at least one phospholipid, said at least one amphoteric surfactant, and said at least one nonionic surfactant are present in a combined amount sufficient to allow said water-insoluble polymer to be incorporated into said aqueous solution; and
applying said aqueous solution to said keratinous substance.

48. A method according to claim 47, wherein said treating comprises a treatment selected from shampooing, conditioning, dyeing, bleaching, permanent waving, relaxing, setting, moisturizing, making-up.

49. A method according to claim 47, wherein said keratinous substance is selected from hair, skin, and eyelashes.

50. A method according to claim 47, wherein making-up comprises a treatment selected from applying mascara to the eyelashes and applying foundation to facial skin.

51. A hair protecting composition comprising:
at least one phospholipid capable of forming bilayers in aqueous solution;
at least one amphoteric surfactant;
at least one nonionic surfactant present in an amount by weight equal to or greater than the amount of said at least one phospholipid;
at least one polyhydroxystyrene polymer; and
an aqueous phase,
wherein said at least one phospholipid, said at least one amphoteric surfactant, and said at least one nonionic surfactant are present in a combined amount sufficient to allow said at least one polyhydroxystyrene polymer to be incorporated into said hair protecting composition.

52. A hair protecting composition according to claim 51, wherein said at least one phospholipid capable of forming bilayers in aqueous solution is a lecithin.

53. A hair protecting composition according to claim 51, wherein said at least one phospholipid, said at least one amphoteric surfactant, and said at least one nonionic surfactant are present in a ratio of 1:1.2:4 and above.

54. A hair protecting composition according to claim 51, wherein said at least one nonionic surfactant is PEG-20 isocetyl ether.

55. A hair protecting composition according to claim 51, wherein said at least one amphoteric surfactant is disodium cocamphodipropionate.

56. A hair protecting composition according to claim 51, wherein said at least one polyhydroxystyrene polymer comprises at least one p-hydroxystyrene monomeric residue and wherein said at least one polyhydroxystyrene polymer is selected from linear, branched, and linear and branched polymers.

* * * * *

UNITED STATES PATENT AND TRADEMARK OFFICE
CERTIFICATE OF CORRECTION

PATENT NO. : 6,436,436 B1
DATED : August 20, 2002
INVENTOR(S) : Nghi Van Nguyen et al.

It is certified that error appears in the above-identified patent and that said Letters Patent is hereby corrected as shown below:

Title page,
Item [57], ABSTRACT,
Lines 3-4, delete "present in an amount by weight equal to or greater than the amount of the phospholipid".

Column 2,
Lines 42-43, "The amphoteric surfactant and nonionic surfactant are each" should read -- The nonionic surfactant is --.
Lines 55-56, "The amphoteric surfactant and nonionic surfactant are each" should read -- The nonionic surfactant is --.

Column 3,
Lines 13-14, delete "present in an amount equal to or greater than the amount of the organic phospholipid".

Column 4,
Lines 26-27, "amphoteric surfactant and nonionic surfactants are each" should read -- nonionic surfactant is --.

Column 5,
Line 10, after "suitable.", insert -- Amphoteric surfactants are typically available for commercial sale in solution form with the active surfactant accounting for approximately 40% of the total solution weight. --.
Line 14, after "Rhône-Poulenc.", insert -- MIRANOL is sold in solution form with amphoteric surfactants composing approximately 40% of the total solution weight. --.
Line 15, after "Croda.", insert -- CROSULTAINE is also sold in solution form with the amphoteric surfactant composing approximately 50% of the total solution weight. --.
Line 18, after "McIntyre Group Ltd.", insert -- , which is a solution with amphoteric surfactants composing approximately 39% of the total solution weight. --.
Line 20, after "Group Ltd.", insert -- , which is a solution with amphoteric surfactants composing approximately 34.5% of the total solution weight. --.
Lines 57-58, delete "and the amphoteric surfactant are each", and insert -- is --.
Line 66, "1:2:2" should read -- 1:0.8:2 --.

UNITED STATES PATENT AND TRADEMARK OFFICE
CERTIFICATE OF CORRECTION

PATENT NO. : 6,436,436 B1
DATED : August 20, 2002
INVENTOR(S) : Nghi Van Nguyen et al.

It is certified that error appears in the above-identified patent and that said Letters Patent is hereby corrected as shown below:

Column 6,
Line 2, "1:2:2" should read -- 1:0.8:2 --.
Line 5, "1:3:3" should read -- 1:1.2:3 --.
Line 6, "1:3:4" should read -- 1:1.2:4 --.
Line 16, "5:15:20 (1:3:4)" should read -- 1:3:4 (which is a LAN ratio of 1:1.2:4) --.
Line 17, after "weight.", insert -- In other words, a LAN ratio of 1:1.2:4 is equal to 10g lecithin, 30g MIRANOL, and 40g ARLASOLVE. --
Lines 36-37, delete "present in an amount greater than or equal to the amount of the phospholipid".
Line 67, delete "when 5% of the organic phospholipid, preferably".

Column 7,
Line 1, delete "lecithin, is used".

Column 9,
Line 50, "1:3:4" should read -- 1:1.2:4 --.

Column 11,
Lines 13-14, "amphoteric surfactant and nonionic surfactant are each" should read
-- nonionic surfactant is --.
Lines 35-36, delete "present in an amount by weight greater than or equal to the amount of the phospholipid".

Column 13,
Lines 35, 36, 56 and 57, "1:3:4" should read -- 1:1.2:4 --.

Column 15,
Lines 55-62, before  insert -- wherein R is --.

Column 18,
Lines 20-27, before  insert -- wherein R is --.

UNITED STATES PATENT AND TRADEMARK OFFICE
CERTIFICATE OF CORRECTION

PATENT NO.      : 6,436,436 B1
DATED           : August 20, 2002
INVENTOR(S)     : Nghi Van Nguyen et al.

It is certified that error appears in the above-identified patent and that said Letters Patent is hereby corrected as shown below:

<u>Column 19,</u>
Line 36, "an said" should read -- and said --.
Line 63, the first occurrence of "(b)" should read -- (c) --.
Line 65, "(c)" should read -- (d) --.
Line 67, "(d)" should read -- (e) --.

Signed and Sealed this

Tenth Day of June, 2003

JAMES E. ROGAN
*Director of the United States Patent and Trademark Office*